US006987176B1

(12) United States Patent
Guerry et al.

(10) Patent No.: US 6,987,176 B1
(45) Date of Patent: Jan. 17, 2006

(54) **COMBINANT POLYPEPTIDE FOR USE IN THE MANUFACTURE OF VACCINES AGAINST *CAMPYLOBACTER* INDUCED DIARRHEA AND TO REDUCE COLONIZATION**

(75) Inventors: Patricia Guerry, Silver Spring, MD (US); Lanfong H. Lee, Silver Spring, MD (US); Edward Burg, Manassas, VA (US); Trevor J. Trust, Sherborn, MA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 09/439,311

(22) Filed: Nov. 12, 1999

Related U.S. Application Data

(60) Provisional application No. 60/108,114, filed on Nov. 12, 1998.

(51) Int. Cl.
C07H 21/02 (2006.01)

(52) U.S. Cl. ............... 536/23.1; 536/23.4; 536/23.7; 514/44; 530/825; 530/403; 435/6; 435/91.1; 435/71.1; 435/69.1; 435/71.2; 435/252.3; 435/252.8; 435/320.1

(58) Field of Classification Search .............. 530/403, 530/402, 825; 435/6, 7, 23, 320.1, 91.2, 435/172.3, 325, 693, 69.1, 71.1, 71.2, 91.1, 435/252.3, 252.8; 514/44; 536/23.1, 24.32, 536/24.33, 23.7, 23.4; 935/77, 78
See application file for complete search history.

(56) References Cited

U.S. PATENT DOCUMENTS

| | | | | |
|---|---|---|---|---|
| 4,801,536 A | * | 1/1989 | Stahl et al. | 435/68 |
| 5,494,795 A | * | 2/1996 | Guerry et al. | 435/6 |
| 5,837,825 A | * | 11/1998 | Meinersmann et al. | 530/403 |
| 5,854,007 A | * | 12/1998 | Ritter et al. | 435/7.23 |
| 5,888,810 A | * | 3/1999 | Meinersmann et al. | 435/320.1 |
| 6,130,082 A | * | 10/2000 | Majarian et al. | 435/252.3 |
| 6,270,974 B1 | * | 8/2001 | Shultz et al. | 435/6 |
| 6,355,435 B1 | * | 3/2002 | Wilson et al. | 435/6 |

OTHER PUBLICATIONS

King, SM et al, Journal of cell science, Dec. 1995, vol. 108(pt 12), pp. 3757-3764 (abstract only).*

(Continued)

*Primary Examiner*—Lynette R. F. Smith
*Assistant Examiner*—Ginny Allen Portner
(74) *Attorney, Agent, or Firm*—Joseph K. Hemby, Jr.; Albert M. Churilla

(57) ABSTRACT

This invention comprises a recombinant protein comprising the maltose binding protein (MBP) of *Escherichia coli* fused to amino acids 5–337 of the FlaA flagellin of *Campylobacter coli* VC167 which has provided evidence of immunogenicity and protective efficacy against challenge by a heterologous strain of *campylobacter, Campylobacter jejuni* 81–176 in mammals. The invention further comprises a recombinant DNA construct encoding the immunodominant region (region I through III) of flagellin from *Campylobacter* spp. for use as a component of a vaccine against *Campylobacter* diarrhea. The invention therefore represents an effective treatment against *Campylobacter* but avoids inducing the autoimmune Guillain Barre Syndrome (GBS), a post-infection polyneuropathy caused by *Campylobacter* molecular mimicry of human gangliosides which has hampered the development of vaccines heretofore.

12 Claims, 4 Drawing Sheets

Figure 1:
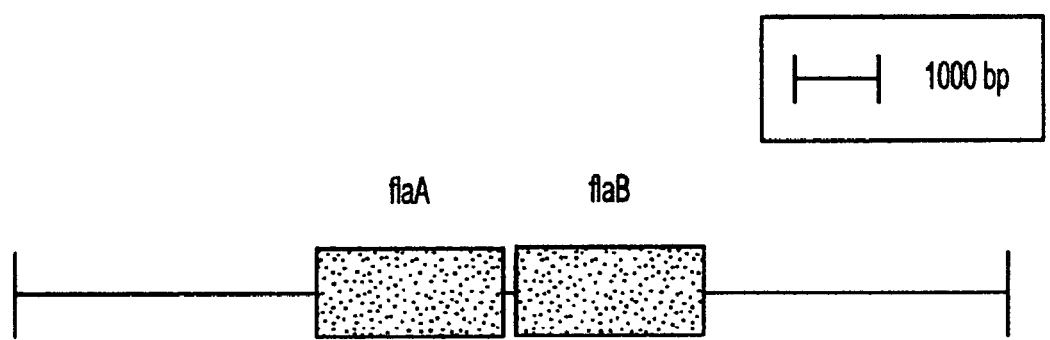
Figure 2:
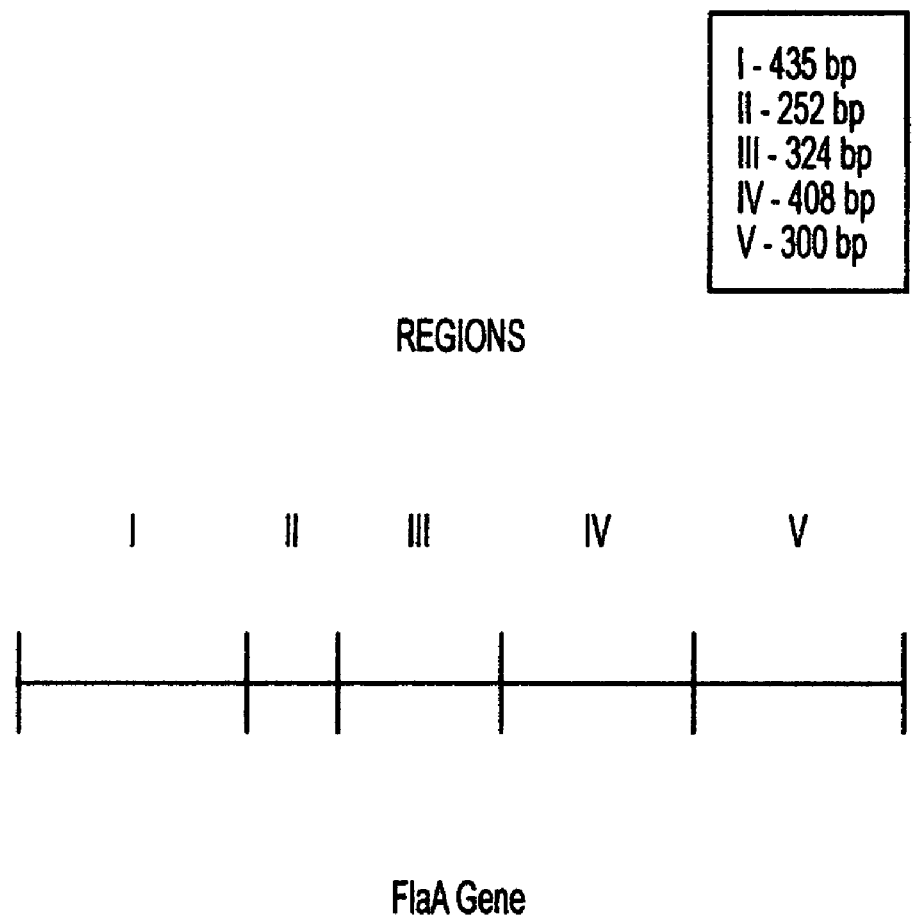

```
I - 435 bp
II - 252 bp
III - 324 bp
IV - 408 bp
V - 300 bp
```

REGIONS

I  II  III  IV  V

FlaA Gene

OTHER PUBLICATIONS

Alm, RA et al, Journal of Bacteriology, vol. 174(13), pp. 4230-4238, Jul. 1992.*

Alm, RA et al, Journal of Bacteriology, vol. 175(10), pp. 3051-3057,. May 1993.*

Alm, RA et al, Journal of Molecular Biology, Mar. 20, 1993, vol. 230(2), pp. 359-363.*

Baqar, S et al, Infection and Immunity, Dec. 1996, vol. 64(12), pp. 4933-4939.*

Doig, P et al, Molecular Microbiology, vol. 19(2), pp. 379-387, Jan., 1996.*

Guerry, P et al, *Campylobacter jejuni* Current status and Future trends, pp. 267-281, 1992, Enteric Dis. Program Nav. Med. Res. Inst, Bethesda, MD, 20814, USA.*

Guerry, P et al, Journal of Bacteriology, vol. 172(4), pp. 1853-1860, Apr. 1990.*

Guerry, P et al, Journal of Bacteriology, vol. 170(1), pp. 316-319, Jan. 1988.*

Guerry, P et al, Molecular Microbiology, vol. 19(2), pp. 369-378, 1996.*

Kanra, G et al, European Journal of paediatric neurology, vol. 1(1), pp. 7-12, 1997.*

Khawaja, Rubine et al, Current Microbiology, vol. 24, pp. 213-221, 1992.*

Khoury, CA et al, Avian Diesases, vol. 39, pp. 812-820, 1995.*

Logan, SM et al, Journal of Bacteriology, vol. 171(6), pp. 3031-3038, Jun. 1989.*

Nuijten, PJM et al, Infection and Immunity, Vo. 59(3), Mar. 1991, pp. 1100-1105.*

Nuijten, PJ et al, Journal of Biol. Chem. Oct. 15, 1990, vol. 265(29), pp. 17,798-17804.*

Power, ME et al, J. of Bacteriology, vol. 176(11), pp. 3303-3313, Jun. 1994.*

Rasmussen, HN et al, Letters in Applied Microbiology, vol. 23, pp. 363-366, 1996.*

Scott, A et al, Infection and Immunity, vol. 58(8), pp. 2686-2689, Aug. 1990.*

Winstanly, C et al, Microbiology-UK, 1997, vol. 143, Oct. 10, 1997, pp. 3071-3084.*

Yao, R et al, Molecular Microbiology, vol. 14(5), pp. 883-893, 1994.*

Yao, R et al, Gene, vol. 130 (1) Aug. 16, 1993, pp. 127-130.*

Lee, LH et al, Infection and Immunity, Nov. 1999, vol. 67(11), pp. 5799-5805.*

Nuijten, PJM et al, The Journal of Biological Chemistry, vol. 265(29), Oct. 15, 1990, pp. 177798-17804.*

Pryor, KD et al, Protein Expression and Purification, 1997, Aug. vol. 10(3), pp. 309-319.*

Dumitru, Ioana, M.SC. 1995, Construction of a *Salmonella typhimurium* strain expressing the *Campylobacter jejuni* flaA gene. vol. 34(2), University of Toronto, Canada.*
Report and Recommendation of the Panel to Assess the NIH investment in Research on Gene Therapy, Orkin et al, Dec. 7, 1995.*
Lee et al. "Evaluation of a Truncated Recombinant Flagellin Subunit Vaccine against *Campylobacter jejuni*". Nov. 1999. Amer. Society for Microbiology. pp. 5799-5805.

* cited by examiner

```
VC167 T2    1   MGFRINTNVAALNAKANSDLNSRALDQSLSRLSSGLRINSAADDASGMAIADSLRSQANTLGQAISNGNDALGIL  75
81-176      1   MGFRINTNVAALNAKANSDLNSRALDQSLSRLSSGLRINSAADDASGMAIADSLRSQANTLGQAISNGNDALGIL  75
                ***************************************************************************

VC167 T2   76   QTADKAMDEQLKILDTIKTKATQAAQDGQSLKTRTMLQADINRLMEELDNIANTTSFNGKQLLSGGFTNQEFQIG  150
81-176     76   QTADKAMDEQLKILDTIKTKATQAAQDGQSLKTRTMLQADINRLMEELDNIANTTSFNGKQLLSGGFTNQEFQIG  150
                ***************************************************************************

VC167 T2  151   SSSNQTIKASIGATQSSKIGVTRFETGSQSFSSGTVGLTIKNYNGIEDFKFQNVVISTSVGTLGLAEEINRNA   225
81-176    151   SSSNQTIKASIGATQSSKIGVTRFETGSQSFSSGTVGLTIKNYNGIEDFKFQNVVISTSVGTLGLAEEINRNA   225
                ***************************************************************************

VC167 T2  226   DKTGIRATFDVKSVGAYAIKAGNTSQDFAINGVVIGKVDYSDGDENGSLISAINAVKDTTGVQASKDENGKLVLT  300
81-176    226   DKTGIRATFDVKSVGAYAIKAGNTSQDFAINGVVIGQINYNDGDMNGQLISAINAVKDTTGVQASKDENGKLVLT  300
                *************************************.. . ********************************

VC167 T2  301   SADGRGIKITGSIGVGAGILHTENYGRLSLVKNDGRDININISGTGLSAIGMGATDMISQSSVSLRESKQISAANA  375
81-176    301   SADGRGIKITGSIGVGAGILHTENYGRLSLVKNDGRDININISGTGLSAIGMGATDMISQSSVSLRESKQISAANA  375
                ***************************************************************************

VC167 T2  376   DAMGFNAYNGGG-AKQIIFASSIAGFMSQAGSGFSAGSGFSVGSGKNYSAILSASIQIVSSARSISSTYVVSTGS   449
81-176    376   DAMGFNSYKGGGKFVFTQNVSSISAFMSAQGSGFSRGSGFSVGSGKNLSVGLSQGIQIISSAASMSNFYVVSAGS   450
                ******.*. ***               ***. *** ***** *** ** .* *. * ****** .**.

VC167 T2  450   GFSAGSGNSQFAALRISTVSAHDETAGVTTLKGAMAVMDIAEFAITNLDQIRADIGSVQNQITSTINNITVTQVN  524
81-176    451   GFSSGSGNSQFAALKTTAANTTDETAGVTTLKGAMAVMDIAEFAITNLDQIRADIGSIQNQVTSTINNITVTQVN  525
                ***.*********. .. . ************************************.*** ************

VC167 T2  525   VKSAESQIRDVDFASESANYSKANILAQSGSSVAMAQANSSQQNVLRLLQ  573
81-176    526   VKAAESQIRDVDFASESANYSKANILAQSGSSVAMAQANSSQQNVLRLLQ  574
                **.***********************************************

FIG. 3
```

COMBINANT POLYPEPTIDE FOR USE IN THE MANUFACTURE OF VACCINES AGAINST *CAMPYLOBACTER* INDUCED DIARRHEA AND TO REDUCE COLONIZATION

CROSS REFERENCE TO RELATED PATENTS AND APPLICATIONS

This application is related to the Provisional Application for Patent entitled, "A Recombinant Polypeptide For Use In The Manufacture of Vaccines Against *Campylobacter* Induced Diarrhea filed Nov. 12, 1998 by the inventors Patricia Guerry, Edward Burg, Lanfong H. Lee, and Trevor J. Trust, and having Ser. No. 60/108,114, and is entitled to the benefit of the Nov. 12, 1998 filing date for the matter disclosed therein. That Provisional Application for Patent is incorporated herein by reference.

BACKGROUND OF THE INVENTION

1. Field of the Invention

The present invention relates to a construct of a recombinant DNA containing a fragment of a bacterial gene and the expression of the constructs for use as a vaccine or a component of a vaccine. Moreover, the invention relates to a recombinant protein comprising the maltose binding protein (MBP) of *Escherichia coli* fused to amino acids 5–337 of the FlaA flagellin of *Campylobacter coli* VC167.

2. Description of the Prior Art

The genus *Campylobacter* are gram-negative, curved, spiral or S-shaped or, in some cases, coccoid, bacteria. *Campylobacter* have a single polar, unsheathed flagellum at one or both ends which imparts a characteristic darting or cork-screw motility. *Campylobacter* are a major cause of gastroenteritis in both developed and developing countries (1,2). The major enteric pathogens in the genus are *C. jejuni* and *C. coli*. All can be normally present in the gastrointestinal tract of domestic and wild animals which act as a major reservoir for infection in humans. Human infection with *Campylobacter* occurs via:

1) animal to human contact especially farm animals such as poultry;
2) human to human transmission especially from infected children;
3) food contamination;
4) water contaminated with excreta from animals.

*Campylobacter* infection can produce both an inflammatory diarrhea and a non-inflammatory diarrhea. The infection is more likely to be of the non-inflammatory type, without fever or bloody diarrhea. However, severe bloody diarrhea resembling bacillary dysentery can occur and frequently is seen in travelers to developing countries.

Although *Campylobacter* diarrhea is treatable with antibiotics, an effective vaccine against the organism is much preferred. This is especially true for travelers to regions where the disease is endemic and for use by developing nations where antibiotics are not always available or where their cost prohibits their use by the general population. There are, however, no currently licensed vaccines available against these organisms.

An important, possible contraindication of whole cell *Campylobacter* vaccine is the potential for development of Guillain-Barre Syndrome (GBS) (3), a post-infectious polyneuropathy, in vaccinated individuals. There are several reports indicating that prior infection with *C. jejuni* can result in acquisition of immunity (10,11). However, development of vaccines has been hampered by a lack of understanding of the basic virulence mechanisms and by the antigenic complexity of these organisms. For example, the serotyping scheme developed by Lior (12) is based on heat labile (HL) antigens and has over 100 recognized serogroups. The heat stable serotyping scheme of Penner (41), which is thought to be based on lippolysaccharides (LPS), has over 70 serotypes. The LPS cores of many serotypes have been shown to contain sialic acid in structures which resemble human gangliosides (13). This molecular mimicry has been implicated in development of autoantibodies leading to GBS, although the specific structure or structures which enable a given *campylobacter* strain to cause GBS are not clear. Strain 81–176 belongs to Serogroup O:23,36. Strains of O:23 and O:36 have been shown to contain ganglioside-like structures in their lipopolysaccharides. Although some O serotypes of *C. jejuni* are implicated with inducing GBS, O serotyping alone is insufficient in determining the potential for a given strain to induce GBS. Also, there is insufficient information to determine definitively the ability of any *Campylobacter* strain to lead to development of GBS.

A formalin fixed whole cell vaccine of *C. jejuni* 81–176 adjuvanted with mutant *E. coli* heat labile enterotoxin (LT$_{R192G}$; 12) is currently in human testing (14,15). This formulation appears to offer protection against homologous challenge in animal models (23,9), but the ability to protect against multiple serotypes of *C. jejuni* remains to be determined. Moreover, given the lack of understanding about the pathogenesis of *Campylobacter* associated GBS, there are concerns about use of whole cell preparations of *campylobacter* as vaccines. This concern becomes more compelling if multiple strains, which are less well characterized than 81–176, were to be combined in order to generate broad cross-serotype specific protection. An alternate approach would be to utilize a single *campylobacter* protein, either as a recombinant subunit vaccine or expressed in a carrier vaccine strain, to elicit protection against multiple serotypes of *Campylobacter*. Therefore, there exists in the current state-of-the-art, the question whether specific *Campylobacter* strains, used in whole-cell vaccines or whole-cell vaccine candidates, could potentiate GBS and therefore be safe for vaccine use. One candidate for inclusion into such vaccines is flagellin.

Flagellin is a component of flagella, which provides swimming motility on many bacterial species including *Campylobacter*. Flagellin is the immunodominant antigen recognized during human and experimental animal infections (16,17,18) with *Campylobacter*. The structure of flagellin has been determined experimentally using the *Campylobacter coli* strain VC167 as a model. The flagella of this organism is complex, composed of multiple species of flagellin subunits, FlaA and FlaB (4–6). The FlaA and FlaB subunits are encoded by two genes, flaA and flaB, that are located adjacent to one another in a tandem orientation (FIG. 1). The expression of these genes is concomitant and unit length rather than polycistronic. The flaA flagellin gene, which encodes the major flagellin subunit in the complex flagellar filament, has been divided into five regions (5) based on restriction enzyme mapping. Regions I–III encode the most highly conserved regions of the protein among different *Campylobacter* flagellin genes and are also the most immunodominant region of the protein (7).

Because of the potentially harmful effects of using whole-cell *Campylobacter* vaccines, it was concluded that an effective vaccine against this organism was needed that, at the same time, did not induce the deleterious autoimmune responses.

SUMMARY OF THE INVENTION

Accordingly, an object of this invention is a recombinant construct and expressed protein possessing highly immunogenic regions of the flagellar subunit but which did not contain antigenic moieties which induce GBS.

Another object of this invention is a recombinant protein, encoded by a portion of the flaA flagellin gene of *Campylobacter coli* VC167 consisting essentially of nucleotides 1–999 of SEQ ID NO.: 1 and corresponding to amino acid residues 1–333 of the amino acid sequence of SEQ ID NO: 238.

Yet another object of the invention is a product that can be expressed in different host backgrounds of bacterial strains belonging to the family Enterobacteriaceae for use in different vaccine formulations against *Campylobacter.*

An additional object of this invention is the induction of a host immune response by purified recombinant flagellin expressed in *E. coli.*

A further object is the cross-reactivity of antibodies, induced by purified recombinant flagellin expressed in *E. coli*, with flagellins from *C. coli* (VC167) and other strains of *Campylobacter* spp.

Another object is that the purified recombinant flagellin expressed in *E. coli* is capable of protecting animals from disease and intestinal colonization by a heterologous strain, *Campylobacter jejuni* 81–176.

A still further object is the use of the construct in vaccine preparations against diarrhea yet reducing the potential for GBS.

Another object is the use of the contstruct in vaccine preparations in order to reduce intestinal colonization.

These and other objects of the invention are accomplished by a recombinant DNA construct encoding the immunodominant region (regions I through III) of flagellin from *Campylobacter* spp. for use as a component of a vaccine against *Campylobacter* disease.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

FIG. 1 is a schematic representation of the flaA and flaB genes of *C. coli*, VC167, which encodes the major flagellin subunits in the flagellar filament.

FIG. 2 is a schematic representation of the regions I through V of flaA. The size, in nucleotide base pairs, of each region is shown. The immunodominant regions are regions I, II and III.

FIG. 3 is a comparison of the amino acid sequences of flagellins flaA of *Campylobacter coli* VC167T2 (SEQ ID NO:6) and *Campylobacter jejuni* 81–176 (SEQ ID NO:5).

FIG. 4 is a graph of the experiment evaluating the ability of MBP-flaA to protect against colonization following oral feeding of mice.

DETAILED DESCRIPTION

Currently, no efficacious vaccine exists for *Campylobacter* disease. The potential for GBS complicates using attenuated strains of *Campylobacter* as a vaccine. It is critical therefore, that a vaccine be produced that is both capable of eliciting a vigorous protective immune response but does not lead to GBS.

Sub-unit vaccines hold a great deal of promise in fulfilling both these important criteria. One of the most highly immunogenic exposed regions of *Campylobacter* is the flagellin proteins, in particular the products of the genes flaA and flaB. The flaA gene of *Campylobacter* has been divided into five regions (5) based on restriction enzyme maps. This region of the flaA gene contains both highly conserved and variable regions among *Campylobacter* species. The preferred embodiment of this invention encompasses the gene sequence and expression from 13 through 1,015 base pairs of the flaA gene of *C. coli* (6), covering regions I, II and III as shown in FIG. 2, and segments within this region. This gene sequence is used to produce a recombinant *Campylobacter* polypeptide, which if introduced into a host is capable of producing an immunological response. The FlaA flagellin is the major protein subunit comprising the flagella filament or locomotory organelle of *Campylobacter* spp.

Region I of the flaA gene represents the highly conserved N terminal region, and regions II and III represent two regions which are more variable among different sequenced flagellin genes. Regions II and III are not, however, as variable as region IV. The construct was made by amplifying the regions I, II and III using the primer flaA-11 (5'ACCAATATTAACACAAATGTTGCAGCA3') (Seq. ID no. 3) and flaA-2 (5'TTATCTAGACTAATCTCTACCATCATTTTTAAC3') (Seq. ID no.4). The PCR product is digested with the appropriate restriction enzymes in order to insert the product into an expression vector. Any plasmid expression vector, e.g. PET™ (Novogen, Madison Wis.) or PMAL™ (New England Biolabs, Beverly, Mass.) and viral expression vectors (e.g. adenovirus, M13, herpesvirus, vaccinia, baculovirus, etc) expression systems can be used as long as the polypeptide is able to be expressed. The PET™ vector is used for the cloning and over-expression of recombinant proteins in *E. coli*. In the PET™ system, the cloned gene is expressed under the control of a phage T7 promotor. In the PMAL™ protein fusion and purification system, the cloned gene is inserted into a PMAL™vector downstream from the MALE™ gene, which encodes maltose-binding protein (MBP). This results in the expression of an MBP-fusion protein. The technique uses the strong $P_{tac}$ promotor and the translation initiation signals of LMBP to express large amounts of the fusion protein. The PMAL-C2™ series of vectors have an exact deletion of the MALE™ signal sequence, resulting in cytoplasmicexpression of the fusion protein. The PMAL-P 2™ series of vectors contain the normal MALE™ signal sequence, which directs the fusion protein through the cytoplasmic membrane, resulting in periplasmic expression. The preferred expression system is the PMAL-C2™ vector (New England Biolabs, Beverly, Mass.). For insertion into this system the PCR product is digested with SspI and XbaI, purified by agarose gel electrophoresis, and cloned in a commercially available plasmid vector, PMAL-P2™ or PMAL-C2™ (New England Biolabs, Beverly, Mass.) which had been digested with XmnI and XbaI. This vector allows for fusion of the fifth codon of the flaA gene to an *Escherichia coli* gene encoding maltose binding protein (MBP). The MBP-FlaA fusion is transcriptionally regulated by a $P_{tac}$ promotor and is induced by growth in isopropylthiogalactoside (IPTG). Several transformants of *E. coli* DH5-alpha, containing plasmids with the appropriate size insert, were sequenced with the MALE™ primer (New England Biolabs). The MALE™ primer is used for sequencing downstream from the malE gene across the polylinker. One plasmid with the expected fusion-protein in the correct reading frame to MALE™, termed pEB11-2, was purified.

The MBP-FlaA fusion protein was purified on the basis of the ability of the MBP portion of the molecule to bind to an amylose affinity column.

Having described the invention, the following examples are given to illustrate specific applications of the invention including the best mode now known to perform the invention. These specific examples are not intended to limit the scope of the invention described in this application.

EXAMPLE 1

Expression of Recombinant flaA Gene in PMAL-P2/C2™ Plasmid.

Purification:

The purification scheme of the construct was as recommended by the commercial supplier of pMal plasmid (New England Biolabs). DH5 alpha containing the flagellin-MBP fusion was grown overnight in 100 ml Rich medium (10 g tryptone, 5 g yeast extract, 5 g NaCl, 2 g glucose/liter) supplemented with 100 microgram/ml, and used to inoculate a fresh 1 liter of the same medium. This culture was grown with shaking at 37° C. to $OD_{600}$ 0.5 and IPTG (isopropyl-B-thiogalactoside) was added to a final concentration of 0.3 mM. Cells were grown for an additional 2 hours and harvested by centrifugation. Cells were resuspended in 10 ml column buffer (20 mM Tris-Cl, 200 mM NaCl, 1 mM EDTA). The cells were frozen at −20° C. overnight, thawed on ice, and sonicated in short pulses for 2 min using a Branson sonicator (Branson, Danbury, Conn.). The sonicated solution was centrifuged for 30 min at 9000 g in a Sorvall RC5-B centrifuge, and the supernatant was diluted 1:5 with column buffer and loaded onto a 2.5×10 cm glass column packed with 15 ml of amylose resin (New England Biolab) at a flow rate of 1 ml/min. The column was washed with 12 volumes of column buffer and the fusion protein was eluted with column buffer containing 10 mM maltose. Protein containing fractions (as determined by BioRad protein assay) were pooled, concentrated using a vacuum concentrator, and stored in aliquots at −20° C.

Characterization:

The apparent $M_r$ of the protein produced by DH5 alpha (pEB1 1–2) after IPTG induction was approximately 80,000, as determined by SDS-PAGE electrophoresis. This is consistent with the predicted $M_r$ of 79,687 for the fusion protein, which includes $M_r$ 34,678 of FlaA and $M_r$ 45,009 from MBP. The fusion protein was immunoreactive with two hyperimmune rabbit antiserum made against flagellin purified from two strains of *Campylobacter*: antiserum E288 which was made against purified flagellin from the homologous strain, *C. coli* VC167 (8) and antiserum SML2 which was made against purified flagellin from *C. jejuni* strain VC74 (9).

Antibody from natural infections was shown to recognize the native protein better than the recombinant protein as shown in Table 2.

Electrophoresis and Western Blotting. SDS-PAGE was performed with a mini-slab gel apparatus (Pharmacia, Piscataway, N.J.) by the method of Laemmli (19). Proteins samples solubilized in sample buffer (21) were separated in 12.5% acrylamide (150V) and either stained with Coomasie brilliant blue or transferred to nitrocellulose for immunological detection (20). Rabbit hyperimmune sera E288 against SDS-denatured VC167 T2 flagellin has been described previously (7). Immunodetection was described in Power et al. (7). The secondary antibody for rabbit antisera was alkaline phosphatase tagged goat anti-rabbit IgG (Caltag, Burlingame, Calif.) used at a final dilution of 1:5000; the secondary antibody for ferret antisera was horse radish peroxidase (HRP) labelled goat anti-ferret IgG (Kirkegaard and Perry, Gaithersburg, Md.) used at a dilution of 1:500. Alkaline phosphatase tagged antibodies were developed with NBT-BCIP (Nitro Blue Tetrazolium, 5-bromo-4chloro-3-indolylphosphate; Promega, Madison, Wis.) and peroxidase labelled antibodies were developed with TMB (3,3',5,5' tetramethyl benzidine; Sigma, St. Louis, Mo.).

Purification of flagellin. Flagellins were purified from *Campylobacter* spp. by the method of Power et al. (37).

Immune animal sera. Immune ferret sera were obtained from a collection of sera at NMRC/FDA from experiments in which ferrets were fed either VC167 T2 or 81–176 and subsequently developed diarrhea (21,22) as shown in Table 2.

Immune human sera. Immune human sera from volunteers fed 81–176 was the generous gift of David Tribble of NMRC.

Hyperimmune rabbit antiserum. Antiserum against the MBP-FlaA in 1 ml Freund's incomplete adjuvant 2 weeks later. The animal was exsanguinated two weeks after the second injection and the resulting antiserum was called LL 1.

ELISA. MaxiSorp 96-well immunoplates were coated with MBP-FlaA or flagellins purified from campylobacters (0.3 micrograms/mL 100 ul/well). ELISA's were performed as previously described (23).

DNA sequence analysis of the flaA gene of *C. jejuni* 81–176. The flaA gene of *C. jejuni* 81–176 has been cloned previously and the 5'end partially sequenced (24). The intact flaA gene of 81–176 as cloned in pK2–32 (24) was sequenced in order to determine the extend of similarity between the VC167 FlaA protein and that of 81–176 which would represent the challenge strain in protection experiments. The results indicate that the flaA gene of 81–176 encodes a protein of 574 amino acids with a predicted $M_r$ of 59,240. Overall the two proteins are 92% identical and 94% similar. VC167 T2 flagellin has 573 amino acids with a predicted $M_r$ of 59,047. The region of the VC167 T2 FlaA which is included in the MBP-FlaA recombinant protein is amino acids 5–337. The region includes those amino acids which appeared to be the most immunogenic by memeotope analysis. The VC167 and 81–176 flagellins are 98.1% identical and 98.7% similar in this region. The homology is lowest between amino acids 382 and 471. In this region, which includes an additional amino acid in the 81–176 protein, the two flagellins are 73% identical and 84% similar. Comparison of the region of VC167 T2 flagellin in the MBP-FlaA fusion protein with 11 other *C. jejuni* flagellins revealed a range of 82–90% similarity. See FIG. 3.

EXAMPLE 2

Use of Recombinant Flagellin to Induce an Immune Response in Rabbits.

Antibodies against the recombinant MBP-FlaA fusion protein are generated in rabbits by injecting rabbits intramuscularly with two (2) doses of 80 micrograms/rabbit for each dose of MBA-FlaA, the first with Freund's complete adjuvant and the second with freund's incomplete adjuvant, two (2) weeks apart. This anti-MBP-FlaA anti-serum reacted with the MBP-FlaA, MBP alone, and with flagellins isolated from both *C. coli* strain VC167 and the *C. jejuni* strain 81–176.

EXAMPLE 3

Use of Recombinant flaA Construction for Production of Subunit Vaccine in the Protection of Mice against *Campylobacter* Disease with or without *E. Coli* Enterotoxin (LT) as Adjuvant.

*Campylobacter* spp. are primarily pathogens of primates and does not cause diarrheal disease when fed to mice. However, when infected intranasally with *Campylobacter* mice develop a lung infection, often with bacteremia, and swallow enough bacteria to become colonized in their gastrointestinal tract (9). This model has been used previously to evaluate vaccines against *campylobacter.*

BALB/c mice (6–8 weeks old) were purchased from Jackson Laboratory (Bar Harbor, Me.) and housed in laminar flow cages for a minimum of 8 days before being used in experiments. Standard laboratory chow and water were provided ad libitum. Mice were anaesthetized with methoxyflurane (Metofane, Pitman-Moore, Mundelein Ill.) and immunized intranasally with 30–35 micrograms/l of fusion protein using a micropipet. The doses used were 0, 3, 6, 12, 25 or 50 micrograms of fusion protein in PBS, either with or without 5 ug of heat labile *E. coli* enterotoxin (LT) as adjuvant. A second dose was administered 8 days after the first vaccination. Intestinal lavage was collected 15 days after the first vaccination and blood was collected 29 days after the first vaccination. The mice were challenged intranasally with *C. jejuni* 81–176 ($2 \times 10^9$/mouse) 34 days after the first vaccination, and the animals were monitored for sickness and death for 5 days. An illness was determined by assigning a score of 0 (healthy), 1 (ill as determined by a hunched back, ruffled fur, lethargy) or 2 (death) for each mouse daily. For each observation day the total score within each group was divided by the number of mice observed to yield the daily index. Fecal pellets were collected daily for 10–14 days after challenge, homogenized in PBS, and plated onto a *campylobacter* selective agar (CVA; Remel, Lenexa, Kans.). Putative *campylobacter* colonies were confirmed by morphology and oxidase reactions. Vaccine efficacy was calculated as (rate for control mice)–(rate for vaccinated mice)/(rate for control mice)×100.

The effect of the vaccine on disease symptoms and colonization are summarized in Table 1. The mean disease index on day 5 of mice which received no vaccine was 0.924 and for mice which received only LT was 0.859. The disease index of mice receiving MBP-FlaA without adjuvant decreased as the dose of vaccine increased up to 50 micrograms (disease index=0.371, reflecting 55.3% efficacy). In all cases the addition of LT decreased the disease index compared to the corresponding dose of MBP-FlaA without LT. A dose of 50 micrograms of MBP-FlaA achieved an 81% efficacy in protection against disease. In previous experiments, infection of mice with live 81–176 resulted in 71% efficacy against disease symptoms following a second challenge with the same.

There was no effect on the numbers of mice colonized with 81–176 at any dose of MBP-FlaA without LT, except at the highest dose (50 micrograms) which showed 47.6% efficacy against colonization. Similarly, mice receiving 3 micrograms, 6 micrograms or 12 micrograms of MBP-FlaA+LT showed no significant reduction in colonization. However, doses of 25 micrograms or 50 micrograms of MBP-FlaA+LT resulted in 61% and 84% efficacy against colonization, respectively. In previous experiments, infection of mice with live 81–176 resulted in 91% efficacy against colonization following a second challenge with the same strain.

The FlaA component of the MBP-FlaA fusion protein is capable of eliciting an immune response which can give significant protection against disease symptoms by a heterologous strain of *Campylobacter* as measured in this animal model, as well as against colonization of the intestine. Protection against colonization would preclude development of diarrheal disease. The regions of the FlaA protein from *C. coli* VC167 which are conserved in the portion of the protein used in these experiments are apparently sufficient to elicit protection against heterologous challenge by *C. jejuni* 81–176. This recombinant construction could be (1) used as a fusion protein, as in the example given here, to MBP, (2) be purified via another recombinant construction as a protein of approximate $M_r$ of 35,000, expressed in another expression system, such as a histidine-tag vector system, or (3) be expressed under control of an appropriate promoter in a carrier vaccine strain such as *Salmonella* or *Shigella* attenuated live vaccines, for use as a bivalent vaccine.

Genbank accession number. The DNA sequence of the 81–176 flaA gene has been deposited in Genbank under accession number AF15052.

EXAMPLE 4

Evaluation of Immunogenicity and Efficacy of the MBP-FlaA Protein Against Heterologous Challenge in the Mouse Intranasal Model.

Mice were immunized intranasally with 2 doses of 3–50 micrograms of MBP-FlaA with or without 5 micrograms of $LT_{R192G}$ as adjuvant. Table 3 shows the intestinal IgA and serum IgG response to MBP-FlaA as measured by ELISA. The full range of MBP-FlaA doses elicited significant antigen-specific serum IgG responses in vaccinated animals and these responses were enhanced by adjuvant use, with the exception of the highest dose (50 micrograms). In contrast, stimulation of FlaA-specific intestinal secretory IgA (sIgA) responses required immunization with higher does of MBP-FlaA ($\geq 25$ micrograms) or co-administration of lower doses with adjuvant. When given with the adjuvant, as little as 3 micrograms of the MBP-FlaA protein was capable of stimulating a significant antigen-specific sIgA response in immunized animals. In addition, the magnitude of intestinal sIgA responses to the recombinant protein were significantly enhanced in those animals receiving the adjuvanted protein compared to those given MBP-FlaA alone, with the exception of the highest dose.

The mice were challnged intranasally with *C. jejuni* 81–176 ($2 \times 10^9$ bacteria/mouse) 26 days after the second immunization. The effects of the vaccine on disease symptoms and colonization on day 7 are summarized in Table 3. The mean disease index of mice which had received no vaccine or $LT_{R192G}$ alone was 0.92 and 0.85, respectively. The disease index of mice receiving MBP-FlaA without adjuvant decreased as the dose of vaccine increased up to 50 $\mu$g (disease index=0.37, reflecting 55.3% efficacy), although the results were not statistically significant. In all cases, except the 3 microgram dose, the addition of $LT_{R192G}$ decreased the disease index compared to the corresponding dose of MBP-FlaA without $LT_{R192G}$. A dose of 50 microgram of MBP-FlaA+$LT_{R192G}$ achieved 81.1% efficacy in protection against disease (P<0.0001). In previous experiments, when mice which had been infected intranasally with live 81–176 were rechallenged 26 days later with the same strain, there was 71% efficacy against disease symptoms.

There was no effect on the numbers of mice colonized with 81–176 at any dose of MBP-FlaA without LT, except at the highest dose (50 micrograms) which showed 47.6% efficacy in protecting against colonization. Similarly, mice receiving the lower doses of MBP-FlaA+$LT_{R192G}$ showed little to no reduction in colonization. However, a dose of 50 micrograms MBP-FlaA+$LT_{R192G}$ resulted in 84.1% efficacy against colonization (P<0.05). In previous experiments using this model, infection of mice with live 81–176 resulted in 91% efficacy against colonization following a second challenge with the same strain.

EXAMPLE 5

Evaluation of the Ability of MBP-FlaA to Protect Against Colonization Following Oral Feeding of Mice.

Figure 4A:
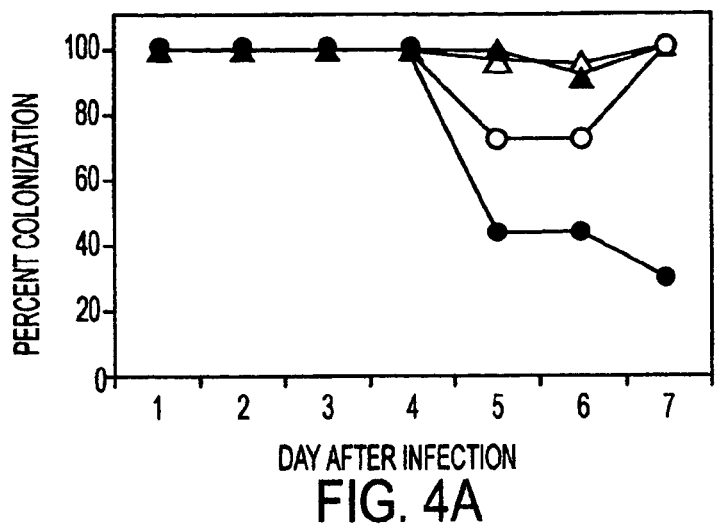
Figure 4B:
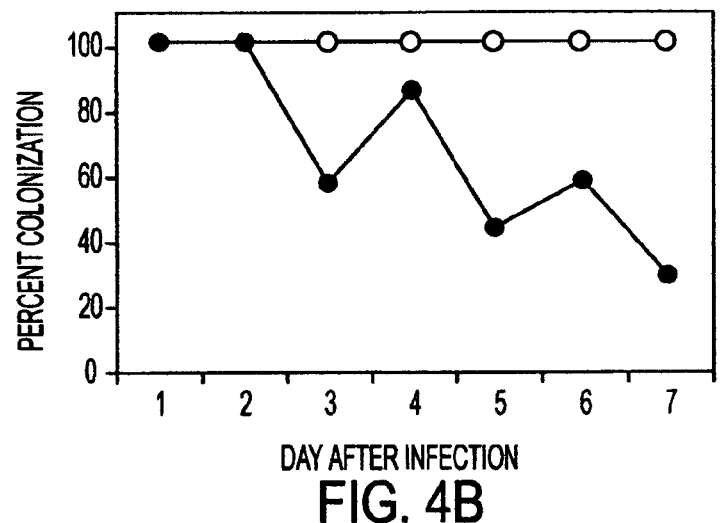
Figure 4C:
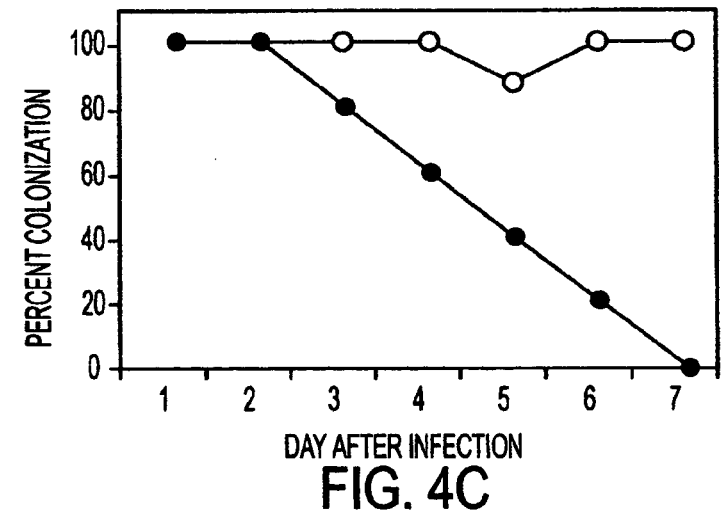

To better examine the ability of MBP-FlaA to protect against intestinal colonization, additional mice were vaccinated with two doses each of 50 micrograms MBP-FlaA with and without 5 micrograms $LT_{R192G}$ adjuvant, 8 days apart. Twenty-six days after the second immunization, groups of 7–8 mice were challenged orally with 3 different doses of 81–176: $8 \times 10^{10}$, $8 \times 10^{9}$ and $8 \times 10^{8}$. Control animals immunized with either PBS (open triangles) or $LT_{R192G}$ (closed triangles) alone were colonized throughout the course of the experiment regardless of challenge dose. These results are shown in FIG. 4A for the highest challenge group only. Animals immunized with MBP-FlaA alone showed an apparent transient and insignificant reduction in total numbers colonized at days 5 and 6 (71.4% of the animals were culture positive) in the high dose challenge group only FIG. 4A. (open circles) However, on day 7 100% of the mice immunized with MBP-FlaA alone were colonized. When animals immunized with MBP-FlaA+$LT_{R192G}$ were challenged with $8 \times 10^{10}$ organisms, there was a marked difference between the controls at days 5–7, with only 40% of the animals being colonized on days 5 and 6 (P<0.05), and 20% colonized on day 7 (P<0.001; FIG. 4A (closed circles). This corresponds to 55.2% efficacy for days 5 and 6, and 71.4% efficacy on day 7. The efficacy improved when the animals were challenged with $8 \times 10^{9}$ bacteria (FIG. 4B). In this case, a significant difference between MBP-FlaA+$LT_{R192G}$ (closed circles) and MBP-FlaA alone (open circles) and control groups was apparent by day 5, with the MBP-FlaA+$LT_{R192G}$ vaccine giving 55.1% efficacy (P <0.05). By day 7 only 28.6% of the animals in this group remained (71.4% efficacy; P<0.001). Challenge of the MBP-FlaA+$LT_{R192G}$ group with $8 \times 10^{8}$ bacteria showed a significant reduction in colonization by day 4 (P<0.05) and a drop in bacterial counts throughout the course of the experiment (FIG. 3C (closed circles). By day 6 the MBP-FlaA+$LT_{R192G}$ vaccine resulted in 78% efficacy against colonization (P 0.001), and by day 7 no campylobacters could be detected in the stools under the sampling conditions used (P<0.001).

The data presented here indicate that MBP-FlaA, when adjuvanted with $LT_{R192G}$ is capable of eliciting a protective immune response against a heterologous strain of campylobacter as measured in two mouse models involving oral and nasal challenge. At the highest dose (50 micrograms MBP-FlaA+5 micrograms $LT_{R192G}$) the vaccine showed 81% protective efficacy against disease and 84% efficacy against colonization of the intestine in the mouse intranasal challenge model (9). In this model immunization with live 81–176, followed by a second infection with the same strain, resulted in 71% efficacy against disease and 91% efficacy against colonization (9). Although the mouse intranasal model uses an unnatural route of infection, it is the only mouse model for campylobacter which consistently results in disease symptoms, generally pneumonia and bacteremia (9). Intestinal colonization presumably occurs in this model when the mice swallow some portion of the infecting bacteria. To more directly measure the protection against colonization, we also challenged mice which had undergone the same immunization regimen (50 micrograms MBP-FlaA+$LT_{R192G}$) with different oral doses of 81–176. The results showed that when challenged with $8 \times 10^{8}$ bacteria, there was a reduction in colonization as early as 3 days after infection and that no campylobacters could be detected in stools 7 days post-feeding.

Flagella are a key virulence determinant of Campylobacter spp. since motility is essential for establishment of colonization in the mucus lining of the gastrointestinal tract (25, 26, 27, 28). Moreover, flagellin is an immunodominant antigen recognized during infection (16, 17,11,18), and it has been suggested that development of antibodies against flagellin correlates with development of protection (29, 11, 18). The observation that feeding of one strain of campylobacter protects against disease from the homologous, but not heterologous strains, (10) is consistent with the idea that the major protective antigen shows variation among strains. Although there is no flagellar serotyping scheme for campylobacters comparable to the H antigen typing scheme of the Enterobacteriaceae, there is serological diversity among campylobacter flagellins (34, 35, 7). In Salmonella and E. coli it has been demonstrated that the amino and carboxy ends of flagellins are involved in transport of the monomer and assembly into the filament, and these regions are highly conserved among serotypes. The central region of the flagellin protein, which lacks functional constraints, is the antigenically diverse region responsible for H serospecificity, and is also the region which is surface exposed in the flagellar filament. Based on comparison of DNA sequence analyses of flagellin genes from several strains of C. jejuni, including that of 81–176 reported here, and one strain of C. coli (4,30, 8, 3, 18, 32), the overall structure of campylobacter flagellins appears similar to those of the enterics. Thus, the amino and carboxy terminal regions are highly conserved among campylobacter flagellins, and the central regions are more variable (36). Moreover, Power et al. (7) have shown that antibodies to the amino and carboxy regions are not surface exposed in the flagella filament of campylobacter. The only antibodies found in that study to be surface exposed in the filament were those which recognize a glycosyl posttranslational modification (33, 37, 38). These modifications alter the apparent $M_r$ of flagellins on SDS-PAGE gels. For example, the masses of the flagellins of VC167 and 81–176 are predicted to differ by only 207, but their apparent difference on SDS-PAGE is greater (see FIG. 1). Moreover, Alm et al. (39) showed that the apparent $M_r$ of flagellin can vary when expressed in different campylobacter hosts. The presence of a carbohydrate moiety on a bacterial flagellin is highly unusual and has been shown to confer serospecificity to the flagellin (33). Thus, antisera which recognize the posttranslational modifications on the flagellar filament of VC167 (Lior 8) also react with flagellins of other strains of Lior 8, but not strains of other Lior serogroups (39). Although flagellin is not the serodeterminant of Lior 8 (i.e. non-flagellated mutants of Lior 8 strains still serotype), flagellins appear to be conserved antigenically within the serogroup. Moreover, more recent studies have suggested that glycosyl modifications on flagellin, as well as other *campylobacter* proteins, are immunodominant (38).

One would expect that any protective epitopes would be surface exposed on the flagellar filament. The role of these surface exposed posttranslational modifications on protection has been addressed in only one study using the removable intestinal tie adult rabbit diarrhea (RITARD) model. In this model protection against colonization appeared to be limited to strains of the same Lior serotype. In other words, immunization by feeding with VC167 protected rabbits against subsequent colonization following RITARD challenge with the homologous strain, as well as two other *C. jejuni* strains of the Lior 8 serogroup, but not against strains of other serogroups (37). A site-specific mutant defective in a gene required for biosynthesis of the posttranslational modification in VC167 was capable of protecting against a challenge of wildtype VC167, but not the other *C. jejuni* Lior 8 strains, suggesting that the posttranslational modifications are responsible for this Lior 8 serospecific protection. Given this data, one would not expect that recombinant flagellin that lacked the posttranslational modifications, which are encoded by other *campylobacter* genes, would be protective, but the data presented here suggest otherwise.

In this regard, it is interesting that antibodies generated during natural infection in ferrets by either 81–176 or VC167 appeared to react more strongly to glycosylated flagellins isolated from *Campylobacter* spp. than to unglycosylated, recombinant flagellins isolated from *E. coli*. Similar analysis using serum from a human volunteer who had been infected with 81–176 (15) also suggested a stronger immune response to native flagellin than recombinant flagellin. This is documented in (40) and is incorporated by reference. Although the recombinant constuction used contains a truncated FlaA, this region was selected based on its high immunogenicity in a mimeotope mapping study (7). Thus, the lack of immune response to this region with antisera from experimentally infected humans and animals was surprising, and suggests that during natural gastrointestinal infection the immunodominant epitopes are those of the posttranslational modifications rather than the primary amino acids. Immunization with the recombinant fusion protein lacking these posttranslational modifications may lead to antibody production against epitopes which are less immunogenic in the native molecule due to differences in folding and/or masking by the carbohydrate moiety, but are, nonetheless, capable of eliciting a protective immune response. We are currently further evaluating this recombinant flagellin as a vaccine in a ferret diarrheal disease model (21, 22).

TABLE 1

Resistance to *C. jejuni* 81-176 challenge following vaccination with recombinant FlaA with or without LT.

| Dose of MBP-FLaA | LT | n | Disease Index | % Efficacy | Fecal Excretion (day 7) % Colonization | % Efficacy |
|---|---|---|---|---|---|---|
| none | − | 13 | 0.924 +/− 0.214 | 0 | 82 | 0 |
| none | + | 11 | 0.859 +/− 0.297 | 7 | 67 | 18.2 |
| 3 ug | − | 7 | 0.771 +/− 0.373 | 16.6 | 100 | 0 |
| 6 ug | − | 7 | 0.771 +/− 0.281 | 16.6 | 100 | 0 |
| 12 ug | − | 7 | 0.743 +/− 0.433 | 18.1 | 100 | 0 |
| 25 ug | − | 12 | 0.483 +/− 0.410 | 44.1 | 92 | 0 |
| 50 ug | − | 7 | 0.371 +/− 0.511 | 55.3 | 43 | 47.6 |
| 3 ug | + | 6 | 0.793 +/− 0.365 | 14.1 | 60 | 26.8 |
| 6 ug | + | 7 | 0.429 +/− 0.378 | 53.6 | 100 | 0 |
| 12 ug | + | 6 | 0.667 +/− 0.391 | 27.8 | 83.0 | 0 |
| 25 ug | + | 12 | 0.333 +/− 0.445 | 64.0 | 77.0 | 61.0 |
| 50 ug | + | 8 | 0.175 +/− 0.244 | 81.1 | 13.0 | 84.0 |

TABLE 2

Serum IgG responses measured by ELISA of ferrets infected with *Campylobacter* spp. to *campylobacter* flagellins and MBP-FlaA.*

| Infecting Strain | Number (%) of animals responding to: | | |
|---|---|---|---|
| | VC167 flagellin | 81-176 flagellin | MBP-FlaA |
| 81-176 | 8/8 (100%) | 8/8 (100%) | 3/8 (37.5%) |
| VC167 T2 | 6/8 (75%) | 7/8 (87.5%) | 3/8 (37.5%) |

*Animals were infected with between $10^9$–$10^{10}$ cells of the indicated strains and serum samples were taken 1 week after infection. An animal was considered to respond to the antigen if there was a greater than 4-fold increase in titer compared to the pre-immune sera.

TABLE 3

Immunogenicity and efficacy of MBP-FlaA given with and without adjuvant in the mouse intranasal model.

| Immunization Regimen | | | Immunogenicity geometric mean titer[#] | | Efficacy at day 7 | | | |
|---|---|---|---|---|---|---|---|---|
| μg MBP-FlaA | $LT_{R192G}$ | n | Lavage IgA | Serum IgG | Disease Symptoms Illness Index | % Efficacy | Fecal Excretion (%) % Colonized | % Efficacy |
| — | − | 13 | 0.9 ± 0 | 5.7 ± 1.2 | 0.92 ± 0.21 | NA | 82* | NA |
| — | + | 11 | 0.9 ± 0 | 4.3 ± 1.3 | 0.86 ± 0.29 | 7.0 | 67* | 18.3 |
| 3 | − | 7 | 1.0 ± 0.3 | 9.9 ± 0.8[a] | 0.77 ± 0.37 | 16.6 | 100 | 0 |
| 6 | − | 7 | 1.3 ± 0.7 | 10.6 ± 1.2[a] | 0.77 ± 0.28 | 16.6 | 100 | 0 |
| 12 | − | 7 | 1.4 ± 0.5 | 10.2 ± 1.6[a] | 0.74 ± 0.43 | 18.1 | 100 | 0 |
| 25 | − | 12 | 3.5 ± 1.0[a] | 11.9 ± 1.9[a] | 0.48 ± 0.41 | 44.1 | 92 | 0 |
| 50 | − | 7 | 5.5 ± 1.1[a] | 14.0 ± 1.5[a] | 0.37 ± 0.51 | 55.3 | 43 | 47.6 |

TABLE 3-continued

Immunogenicity and efficacy of MBP-FlaA given with and without adjuvant in the mouse intranasal model.

| Immunization Regimen | | | Immunogenicity geometric mean titer[#] | | Efficacy at day 7 | | | |
|---|---|---|---|---|---|---|---|---|
| | | | | | Disease Symptoms | | Fecal Excretion (%) | |
| μg MBP-FlaA | $LT_{R192G}$ | n | Lavage IgA | Serum IgG | Illness Index | % Efficacy | % Colonized | % Efficacy |
| 3 | + | 6 | 3.5 ± 0.8[a,c] | 13.2 ± 0.6[a,c] | 0.79 ± 0.37 | 14.1 | 60** | 26.8 |
| 6 | + | 7 | 3.4 ± 0.8[a,c] | 13.1 ± 0.5[a,c] | 0.43 ± 0.38[b] | 53.6 | 100 | 0 |
| 12 | + | 6 | 3.4 ± 1.3[b,d] | 12.8 ± 1.0[a,d] | 0.67 ± 0.39 | 27.8 | 83 | 0 |
| 25 | + | 12 | 5.7 ± 12[a,c] | 14.1 ± 1.7[a,d] | 0.33 ± 0.44[b] | 64.0 | 75 | 8.5 |
| 50 | + | 8 | 6.6 ± 0.6[a,d] | 14.8 ± 0.7[a] | 0.17 ± 0.24[a] | 81.1 | 13[b] | 84.1 |

[#]geometric mean titer is expressed as natural log transformed values.
[a]$P < 0.001$ compared to animals immunized with PBS;
[b]$P < 0.05$ compared to animals immunized with PBS;
[c]$P < 0.001$ compared to animals immunized with a comparable dose of MBP-FlaA without adjuvant;
[d]$P < 0.05$ compared to animals immunized with a comparable dose of MBP-FlaA without adjuvant.
*2 animals died following challenge;
**1 animal died following challenge.

REFERENCES

1. Tauxe, R. V. 1992. Epidemiology of *C. jejuni* infections in the U.S. and other industrial nations, pp 9–19. In I. Nachamkin, M. J. Blaser and L. S. Tompkins (eds), *Campylobacter jejuni*: Current status and future trends. American Society for Microbiology, Washington, D.C.
2. Taylor, D. N. 1992. *Campylobacter* infections in developing countries, pp. 20–30. In I. Nachamkin, M. J. Blaser, and L. S. Tompkins (ed.), *Campylobacter jejuni*: Current status and future trends. Amer. Soc. For Microbiology, Washington, D.C.
3. Kuroki, S., t. Haruta, M. Yoshioka, Y. Kobayaski, M. Nukina, and H. Nakanishi. 1991. Guillain-Barre syndrome associated with *Campylobacter* infection. Pediatr. Infect. Dis. 10:149.
4. Guerry, P., R. A. Alm, M. E. Power, S. M. Logan, and T. J. Trust. 1991. The role of two flagellin genes in *Campylobacter* motility. J. Bacteriol. 173:4757.
5. Guerry, P., R. A. Alm, M. E. Power, and T. J. Trust. 1992. Molecular and structural analysis of *Campylobacter* flagellin, p. 267–281. In. I. Nachamkin, M. J. Blaser, and L. S. Tompkin (ed.), *Campylobacter jejuni: Current Status and Future Trends*. American Society for Microbiology, Washington, D.C.
6. Guerry, P., S. M. Logan, S. Thornton, and T. J. Trust. 1990. Genomic organization and expression of *Campylobacter* flagellin genes. J. Bacteriol. 172:1853.
7. Power, M. E., P. Guerry, W. D. McCubbin, C. M. Kay and T. J. Trust. 1994. Structural and antigenic characteristics of *Campylobacter coli* fla A flagellin J. Bacteriol. 176:3303.
8. Logan, S. M., T. J. Trust, and P. Guerry. 1989. Evidence for postranslational modification and gene duplication of *Campylobacter* flagellin. J. Bacteriol. 171(6):3031.
9. Baqar, S., A. L. Bourgeois, L. A. Applebee, A. S. Mourad, M. T. Kleinosky, Z. Mohran, and J. R. Murphy. 1996. Murine intranasal challenge model for the study of *Campylobacter* pathogenesis and immunity. Inf Imm. 64:4933.
10. Black, R. E., M. M. Levine, M. L. Clements, T. P. Hughes and M. J. Blaser. 1988. Experimental *Campylobacter jejuni* infection in humans. J. Infect Dis. 157:472–479.
11. Martin, P. M., J. Mathiot, J. Ipero, M. Kirimat, A. J. Georges, and M. C. Georges-Courbot. 1989. Immune response to *Campylobacter jejuni* and *Campylobacter coli* in a cohort of children from birth to 2 years of age. Infect. Immun. 57:2542–2546.
12. Lior, H., D. H. Woodward, J. A. Edgar, L. J. Laroche, and P. Gill. 1982. Serotyping of *Campylobacter jejuni* by side agglutination based on heat-labile antigenic factors. J. Clin. Microbiol. 15: 761–768.
13. Moran, A. P., B. J. Appelmelk, and G. O. Aspinall. 1996. Molecular mimicry of host structures by lipopolysaccharides of *Campylobacter* and *Helicobacter* spp.: implications for pathogenesis. J. Endotox Res. 3(6):521–531.
14. Scott, D. A. 1997. Vaccines against *Campylobacter jejuni*. J. Infect. Dis. 176 (Suppl 2): S183–188
15. Tribble, D. Unpublished data.
16. Blaser, M. J. and D. J. Duncan. 1984. Human serum antibody response to *Campylobacter jejuni* infection as measured in an enzyme-linked immunoabsorbent assay. Infect. Immun. 44:297–298.
17. Blaser, M. J., J. A. Hopkin, and M. L. Vasil. 1984. *Campylobacter jejuni* outer membrane proteins are antigenic for humans. Infect. Immun. 43:986–993.
18. Nachamkin, I. And A. M. Hart. 1985. Western blot analysis of the human antibody response to *Campylobacter jejuni* cellular antigens during gastrointestinal infection. J. Clin. Microbiol. 21:33–38.
19. Laemmli, U. K. 1970. Cleavage of structural proteins during the assembly of the head of bacteriophage T4. Nature (London) 227:680–685.
20. Logan, S. M. and T. J. Trust. 1983. Molecular identification of surface protein antigens of *Campylobacter jejuni*. J. Bacteriol. 168:739–745.
21. Doig, P., R. Yao, D. H. Burr, P. Guerry and T. J. Trust. 1996. An environmentally regulated pilus-like appendage involved in *Campylobacter* pathogenesis. Mol. Microbiol. 20(4):885–894.
22. Yao, R., D. H. Burr, and P. Guerry. 1997. Che Y-mediated modulation of *Campylobacter jejuni* virulence. Mol. Microbiol. 23:1021–1032.
23. Baqar, S., A. L. Bourgeois, P. J. Schultheiss, R. I. Walker, D. M. Rollins, R. L. Halberberger, and O. R. Pavlovskis. 1995. Safety and immunogenicity of a prototype oral whole-cell killed *Campylobacter* vaccine adminstered with a mucosal adjuvant in non-human primates. Vaccine 13:22–28.
24. Yao, R., D. H. Burr, P. Doig, T. J. Trust, H. Niu, and P. Guerry. 1994. Isolation of motile and non-motile insertional mutants of *Campylobacter jejuni* defective in invasion of eukaryotic cells: the role of flagella in invasion. Mol. Microbiol. 14(5):883–893.
25. Lee, A, J. L. O'Rourke, P. J. Barrington, and T. J. Trust. 1986. Mucus colonization by Campylobacter jejuni: a mouse cecal model. Infect. Immun. 51:536–546.
26. Morooka, T., A. Umeda, and K. Amaka. 1985. Motility as an intestinal colonization factor for *Campylobacter jejuni*. J. Gen. Microbiol. 131:1973–1980.
27. Pavlovskis, O. R., D. M. Rollins, R. L. Haberberger, Jr., A. E. Green, L. Habash, S. Stroko, and R. I. Walker. 1991. Significance of flagella in colonization resistance of rabbits immunized with *Campylobacter* spp. Infect. Immun. 59:2259–2264.
28. Wassenaar, T. M., B. A. M. Van der Zeijst, R. Ayling, and D. G. Newell. 1993 Colonization of chicks by motility mutants of *Campylobacter jejuni* demonstates the importance of flagellin A expression. J. Gen. Microbiol. 139:1171–1175.
29. Butzler, J.P., Y. Glupczynsk, and Y. Goodson. 1992. *Campylobacter* and *Helicobacter* infections. Curr. Opin. Infect. Dis. 5:80–87.
30. Khawaja, R., K. Neote, H. L. Bingham, J. L. Penner, and V. L. Chan. 1992. Cloning and sequence analysis of the flagellin gene of *Campylobacter jejuni* TGH9011. Curr. Microbiol. 24:213–221.
31. Meinersmann, R. J., L. O. Helsel, P. I. Fields, and K. L. Hiett. 1997. Discrimination of *Campylobacter jejuni* isolates by fla gene sequencing. J. Clin. Microbiol. 35:2810–2814.
32. Nuijten, P. J., F. J. van Asten, W. Gaastra, and B. A. van der Zeijst. 1990. Structural and functional analysis of two *Campylobacter jejuni* flagellin genes. J. Biol. Chem. 265:17798–17804.
33. Doig, P., N. Kinsella, P. Guerry, and T. J. Trust 1996. Characterization of a posttranslational modification of *Campylobacter* flagellin: identification of a serospecific glycosyl moiety. Mol. Microbiol. 19(2):379–387.
34. Harris, L. A., S. M. Logan, P. Guerry, and T. J. Trust. 1987. Antigenic variation of *Campylobacter* flagella. J. Bacteriol. 169:5066–5071.
35. Logan, S. M. and T. J. Trust. 1986. Location of epitopes on *Campylobacter jejuni* flagella. J. Bacteriol. 168:739–745.
36. Homma, M., H. Fujita, S. Yamaguchi, and T Iino. 1987. Regions of *Salmonella typhimurium* flagellin is essential for its polymerization and excretion. J. Bacteriol. 169: 291–296.
37. Guerry, P., P. Doig, R. A. Alm, D. H. Burr, N. Kinsiella, and T. J. Trust. 1996. Identification and characterization of genes required for post translational modification of *Campylobacter coli* VC167 flagellin.
38. Szymanski, C. M., R. Yao, C. P. Ewing, T. J. Trust and P. Guerry. 1999. Evidence for a system of general protein glycosylation in *Campylobacter jejuni*. Mol. Microbiol. (in press)
39. Alm, R. A., P. Guerry, M. E. Power, and T. J. Trust. 1992. Variation in antigenicity and molecular weight of *Campylobacter coli* VC167 flagellin in different genetic backgrounds. J. Bacteriol. 174:4230–4238.
40. Lee, L. H., E. Burg, S. Baqar, A. L. Burgeois, D. H. Burr, C. P. Ewing, T. J. Trust and P. Guerry. Evaluation of Truncated Recombinant Flagellin Subunit Vaccine against *Campylobacter jejuni*. Infect. and Immun. 67:5799–5805.

Obviously, many modifications and variations of the present invention are possible in light of the above teachings. It is therefore to be understood that, within the scope of the appended claims, the invention may be practiced otherwise than as specifically described. Accordingly, the recombinant construct can be used as a fusion protein with not only MBP, described here, but with other protein expression systems. The recombinant construct can also be expressed in carrier vaccines such as *Salmonella* or *Shigella* attenuated, live vaccines, for use as a bivalent vaccine.

What is claimed is:

1. An isolated and purified polynucleotide sequence that is a portion of the flaA coding region of *Campylobacter*, said polynucleotide sequence consisting of nucleotides 1–999 of the DNA SEQ ID NO: 1, and said polynucleotide encoding an immunogenic polypeptide.

2. A recombinant expression vector comprising the polynucleotide of claim 1, wherein said vector comprises said polynucleotide operatively linked for expression in an expression system, wherein said expression vector is selected from the group consisting of plasmid and viral expression vectors.

3. A recombinant expression vector system comprising the recombinant expression vector of claim 2, wherein said expression vector further comprises an *E. coli* gene encoding maltose binding protein, said polynucleotide sequence being fused to said *E. coli* gene.

4. An isolated and purified DNA sequence encoding an immunogenic polypeptide consisting of amino acid residues 1–333 of amino acid sequence of SEQ ID NO:2.

5. A composition comprising:

an isolated and purified polynucleotide sequence consisting of nucleotides 1–999 of SEQ ID NO. 1 encoding an immunogenic polypeptide consisting of amino acid residues 1–333 of SEQ ID NO. 2, wherein said polynucleotide is operatively linked to an expression system selected from the group consisting of plasmid and viral expression vectors and wherein said expression system is capable of being expressed in competent bacterial cells selected from the group consisting of *E. coli, Shigella* and *Salmonella.*

6. The composition of claim 5, wherein said expression system further comprises an *E. coli* gene encoding maltose binding protein, said polynucleotide sequence being fused and operatively linked to said *E. coli* gene.

7. The composition of claim 6, further comprising an adjuvant.

8. The composition of claim 7, wherein said adjuvant is a non-toxigenic form of heat labile *E. coli* enterotoxin.

9. The composition of claim 5 wherein said polypeptide is capable of reducing colonization of *Campylobacter* when administered as a vaccine.

10. A bivalent immunogenic composition comprising a live, attenuated, carrier strain of bacteria, wherein said bacteria is transformed with either a plasmid or viral expression vector system operatively linked to an isolated and purified polynucleotide sequence that is a portion of the flaA coding region of *Campylobacter*, said polynucleotide sequence consisting of nucleotides 1–999 of the DNA SEQ ID NO: 1, said polynucleotide encoding an immunogenic polypeptide consisting of amino acid residues 1–333 of SEQ ID NO 2.

11. The bivalent immunogenic composition of claim 10, wherein said expression system further comprises an *E. coli* gene encoding maltose binding protein, said polynucleotide sequence being fused to said *E. coli* gene and said *E. coli* gene being contained in said expression vector system.

12. The bivalent immunogenic composition of claim 10, wherein said carrier strain comprises *Salmonella* or *Shigella*.

* * * * *

UNITED STATES PATENT AND TRADEMARK OFFICE
CERTIFICATE OF CORRECTION

PATENT NO. : 6,987,176 B1
DATED : January 17, 2006
INVENTOR(S) : Patricia Guerry et al.

It is certified that error appears in the above-identified patent and that said Letters Patent is hereby corrected as shown below:

<u>Title page, Item [54] and Column 1, line 1,</u>
Title, the first word should be -- RECOMBINANT. --.

Signed and Sealed this

Twenty-first Day of March, 2006

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 999
<212> TYPE: DNA
<213> ORGANISM: Campylobacter coli
<220> FEATURE:
<223> OTHER INFORMATION:

<400> SEQUENCE: 1
attaacacaa atgttgcagc attaaatgct aaagcaaatt cggatctaaa cagcagagca      60
ttagatcaat cactttcaag actcagttca ggtcttagaa tcaactccgc agcagatgat     120
gcttcaggga tggcgatagc agatagttta agatctcagg caaatacttt gggtcaggct     180
atatctaatg gtaatgatgc tttaggtatc ttgcaaactg cagataaggc tatggatgag     240
caacttaaaa tcttagatac catcaagact aaagcgactc aagctgctca agatggtcaa     300
agcttaaaaa caagaactat gcttcaagca gacatcaacc gtttgatgga agaacttgat     360
aatatcgcaa ataccacttc atttaatggc aaacaacttt taagtggtgg tttttaccaat     420
```

-continued

```
caagaattcc aaatcggttc aagttcaaat caaactatta aagcaagtat aggagcaact    480
cagtcttcta aaatcggtgt aacaagattt gaaacaggtt cacaaagttt ttcttcaggc    540
actgtaggac ttactattaa aaactacaac ggtatcgaag attttaaatt tgatagtgta    600
gtgatttcta cttcagtagg aacaggtctt ggagctttgg ctgaagagat caacagaaat    660
gcagataaaa caggaattcg tgcaactttt gatgtaaaat ctgtaggagc ctatgcaata    720
aaagcaggaa atacttctca ggattttgct atcaatgggg ttgttatagg taaggttgat    780
tattcagatg gtgatgagaa tggttcttta atttcagcta tcaatgctgt aaaagataca    840
actggtgttc aagcctctaa agatgaaaat ggtaaacttg ttcttacttc ggccgatggt    900
agagggatta aaatcacagg tagcataggt gtaggagctg gtatattgca cactgaaaat    960
tatggaaggt tatctttagt taaaaatgat ggtagagat                            999
```

<210> SEQ ID NO 2
<211> LENGTH: 333
<212> TYPE: PRT
<213> ORGANISM: Campylobacter coli
<220> FEATURE:
<223> OTHER INFORMATION:

<400> SEQUENCE: 2

```
Ile Asn Thr Asn Val Ala Ala Leu Asn Ala Lys Ala Asn Ser Asp
 1               5                  10                  15

Leu Asn Ser Arg Ala Leu Asp Gln Ser Leu Ser Arg Leu Ser Ser
                20                  25                  30

Gly Leu Arg Ile Asn Ser Ala Ala Asp Ala Ser Gly Met Ala
                35                  40                  45

Ile Ala Asp Ser Leu Arg Ser Gln Ala Asn Thr Leu Gly Gln Ala
                50                  55                  60

Ile Ser Asn Gly Asn Asp Ala Leu Gly Ile Leu Gln Thr Ala Asp
                65                  70                  75

Lys Ala Met Asp Glu Gln Leu Lys Ile Leu Asp Thr Ile Lys Thr
                80                  85                  90

Lys Ala Thr Gln Ala Ala Gln Asp Gly Gln Ser Leu Lys Thr Arg
                95                 100                 105

Thr Met Leu Gln Ala Asp Ile Asn Arg Leu Met Glu Glu Leu Asp
               110                 115                 120

Asn Ile Ala Asn Thr Thr Ser Phe Asn Gly Lys Gln Leu Leu Ser
               125                 130                 135

Gly Gly Phe Thr Asn Gln Glu Phe Gln Ile Gly Ser Ser Ser Asn
               140                 145                 150

Gln Thr Ile Lys Ala Ser Ile Gly Ala Thr Gln Ser Ser Lys Ile
               155                 160                 165

Gly Val Thr Arg Phe Glu Thr Gly Ser Gln Ser Phe Ser Ser Gly
               170                 175                 180

Thr Val Gly Leu Thr Ile Lys Asn Tyr Asn Gly Ile Glu Asp Phe
               185                 190                 195

Lys Phe Asp Ser Val Val Ile Ser Thr Ser Val Gly Thr Gly Leu
               200                 205                 210

Gly Ala Leu Ala Glu Glu Ile Asn Arg Asn Ala Asp Lys Thr Gly
               215                 220                 225

Ile Arg Ala Thr Phe Asp Val Lys Ser Val Gly Ala Tyr Ala Ile
               230                 235                 240
```

```
Lys Ala Gly Asn Thr Ser Gln Asp Phe Ala Ile Asn Gly Val Val
                245                 250                 255

Ile Gly Lys Val Asp Tyr Ser Asp Gly Asp Glu Asn Gly Ser Leu
                260                 265                 270

Ile Ser Ala Ile Asn Ala Val Lys Asp Thr Thr Gly Val Gln Ala
                275                 280                 285

Ser Lys Asp Glu Asn Gly Lys Leu Val Leu Thr Ser Ala Asp Gly
                290                 295                 300

Arg Gly Ile Lys Ile Thr Gly Ser Ile Gly Val Gly Ala Gly Ile
                305                 310                 315

Leu His Thr Glu Asn Tyr Gly Arg Leu Ser Leu Val Lys Asn Asp
                320                 325                 330

Gly Arg Asp

<210> SEQ ID NO 3
<211> LENGTH: 27
<212> TYPE: DNA
<213> ORGANISM: Campylobacter coli
<220> FEATURE:
<223> OTHER INFORMATION:

<400> SEQUENCE: 3
accaatatta acacaaatgt tgcagca                                        27

<210> SEQ ID NO 4
<211> LENGTH: 33
<212> TYPE: DNA
<213> ORGANISM: Campylobacter coli
<220> FEATURE:
<223> OTHER INFORMATION:

<400> SEQUENCE: 4
ttatctagac taatctctac catcattttt aac                                 33

<210> SEQ ID NO 5
<211> LENGTH: 574
<212> TYPE: PRT
<213> ORGANISM: Campylobacter jejuni 81-176
<220> FEATURE:
<223> OTHER INFORMATION:

<400> SEQUENCE: 5

Met Gly Phe Arg Ile Asn Thr Asn Val Ala Ala Leu Asn Ala Lys
 1               5                  10                  15

Ala Asn Ser Asp Leu Asn Ser Arg Ala Leu Asp Gln Ser Leu Ser
                20                  25                  30

Arg Leu Ser Ser Gly Leu Arg Ile Asn Ser Ala Ala Asp Asp Ala
                35                  40                  45

Ser Gly Met Ala Ile Ala Asp Ser Leu Arg Ser Gln Ala Asn Thr
                50                  55                  60

Leu Gly Gln Ala Ile Ser Asn Gly Asn Asp Ala Leu Gly Ile Leu
                65                  70                  75

Gln Thr Ala Asp Lys Ala Met Asp Glu Gln Leu Lys Ile Leu Asp
                80                  85                  90

Thr Ile Lys Thr Lys Ala Thr Gln Ala Ala Gln Asp Gly Gln Ser
                95                 100                 105

Leu Lys Thr Arg Thr Met Leu Gln Ala Asp Ile Asn Arg Leu Met
               110                 115                 120

Glu Glu Leu Asp Asn Ile Ala Asn Thr Thr Ser Phe Asn Gly Lys
```

-continued

```
                    125                 130                 135
Gln Leu Ser Gly Gly Phe Thr Asn Gln Glu Phe Gln Ile Gly
                    140                 145                 150
Ser Ser Ser Asn Gln Thr Ile Lys Ala Ser Ile Gly Ala Thr Gln
                    155                 160                 165
Ser Ser Lys Ile Gly Val Thr Arg Phe Glu Thr Gly Ser Gln Ser
                    170                 175                 180
Phe Ser Ser Gly Thr Val Gly Leu Thr Ile Lys Asn Tyr Asn Gly
                    185                 190                 195
Ile Glu Asp Phe Lys Phe Asp Ser Val Val Ile Ser Thr Ser Val
                    200                 205                 210
Gly Thr Gly Leu Gly Ala Leu Ala Glu Glu Ile Asn Arg Asn Ala
                    215                 220                 225
Asp Lys Thr Gly Ile Arg Ala Thr Phe Asp Val Lys Ser Val Gly
                    230                 235                 240
Ala Tyr Ala Ile Lys Ala Gly Asn Thr Ser Gln Asp Phe Ala Ile
                    245                 250                 255
Asn Gly Val Val Ile Gly Gln Ile Asn Tyr Asn Asp Gly Asp Asn
                    260                 265                 270
Asn Gly Gln Leu Ile Ser Ala Ile Asn Ala Val Lys Asp Thr Thr
                    275                 280                 285
Gly Val Gln Ala Ser Lys Asp Glu Asn Gly Lys Leu Val Leu Thr
                    290                 295                 300
Ser Ala Asp Gly Arg Gly Ile Lys Ile Thr Gly Ser Ile Gly Val
                    305                 310                 315
Gly Ala Gly Ile Leu His Thr Glu Asn Tyr Gly Arg Leu Ser Leu
                    320                 325                 330
Val Lys Asn Asp Gly Arg Asp Ile Asn Ile Ser Gly Thr Gly Leu
                    335                 340                 345
Ser Ala Ile Gly Met Gly Ala Thr Asp Met Ile Ser Gln Ser Ser
                    350                 355                 360
Val Ser Leu Arg Glu Ser Lys Gly Gln Ile Ser Ala Ala Asn Ala
                    365                 370                 375
Asp Ala Met Gly Phe Asn Ser Tyr Lys Gly gly Gly Lys Phe Val
                    380                 385                 390
Phe Thr Gln Asn Val Ser Ser Ile Ser Ala Phe Met Ser Ala Gln
                    395                 400                 405
Gly Ser Gly Phe Ser Arg Gly Ser Gly Phe Ser Val Gly Ser Gly
                    410                 415                 420
Lys Asn Leu Ser Val Gly Leu Ser Gln Gly Ile Gln Ile Ile Ser
                    425                 430                 435
Ser Ala Ala Ser Met Ser Asn Thr Tyr Val Val Ser Ala Gly Ser
                    440                 445                 450
Gly Phe Ser Ser Gly Ser Gly Asn Ser Gln Phe Ala Ala Leu Lys
                    455                 460                 465
Thr Thr Ala Ala Asn Thr Thr Asp Glu Thr Ala gly Val Thr Thr
                    470                 475                 480
Leu Lys Gly Ala Met Ala Val Met Asp Ile Ala Glu Thr Ala Ile
                    485                 490                 495
Thr Asn Leu Asp Gln Ile Arg Ala Asp Ile Gly Ser Ile Gln Asn
                    500                 505                 510
Gln Val Thr Ser Thr Ile Asn Asn Ile Thr Val Thr Gln Val Asn
                    515                 520                 525
```

-continued

Val Lys Ala Ala Glu Ser Gln Ile Arg Asp Val Asp Phe Ala Ser
                530                 535                 540

Glu Ser Ala Asn Tyr Ser Lys Ala Asn Ile Leu Ala Gln Ser Gly
            545                 550                 555

Ser Tyr Ala Met Ala Gln Ala Asn Ser Ser Gln Gln Asn Val Leu
            560                 565                 570

Arg Leu Leu Gln

<210> SEQ ID NO 6
<211> LENGTH: 573
<212> TYPE: PRT
<213> ORGANISM: Campylobacter coli VC167 T2
<220> FEATURE:
<223> OTHER INFORMATION:

<400> SEQUENCE: 6

Met Gly Phe Arg Ile Asn Thr Asn Val Ala Ala Leu Asn Ala Lys
 1               5                  10                  15

Ala Asn Ser Asp Leu Asn Ser Arg Ala Leu Asp Gln Ser Leu Ser
                20                  25                  30

Arg Leu Ser Ser Gly Leu Arg Ile Asn Ser Ala Ala Asp Asp Ala
                35                  40                  45

Ser Gly Met Ala Ile Ala Asp Ser Leu Arg Ser Gln Ala Asn Thr
                50                  55                  60

Leu Gly Gln Ala Ile Ser Asn Gly Asn Asp Ala Leu Gly Ile Leu
                65                  70                  75

Gln Thr Ala Asp Lys Ala Met Asp Glu Gln Leu Lys Ile Leu Asp
                80                  85                  90

Thr Ile Lys Thr Lys Ala Thr Gln Ala Ala Gln Asp Gly Gln Ser
                95                  100                 105

Leu Lys Thr Arg Thr Met Leu Gln Ala Asp Ile Asn Arg Leu Met
                110                 115                 120

Glu Glu Leu Asp Asn Ile Ala Asn Thr Thr Ser Phe Asn Gly Lys
                125                 130                 135

Gln Leu Leu Ser Gly Gly Phe Thr Asn Gln Glu Phe Gln Ile Gly
                140                 145                 150

Ser Ser Ser Asn Gln Thr Ile Lys Ala Ser Ile Gly Ala Thr Gln
                155                 160                 165

Ser Ser Lys Ile Gly Val Thr Arg Phe Glu Thr Gly Ser Gln Ser
                170                 175                 180

Phe Ser Ser Gly Thr Val Gly Leu Thr Ile Lys Asn Tyr Asn Gly
                185                 190                 195

Ile Glu Asp Phe Lys Phe Gln Ser Val Val Ile Ser Thr Ser Val
                200                 205                 210

Gly Thr Gly Leu Gly Ala Leu Ala Glu Glu Ile Asn Arg Asn Ala
                215                 220                 225

Asp Lys Thr Gly Ile Arg Ala Thr Phe Asp Val Lys Ser Val Gly
                230                 235                 240

Ala Tyr Ala Ile Lys Ala Gly Asn Thr Ser Gln Asp Phe Ala Ile
                245                 250                 255

Asn Gly Val Val Ile Gly Lys Val Asp Tyr Ser Asp Gly Asp Glu
                260                 265                 270

Asn Gly Ser Leu Ile Ser Ala Ile Asn Ala Val Lys Asp Thr Thr
                275                 280                 285

-continued

```
Gly Val Gln Ala Ser Lys Asp Glu Asn Gly Lys Leu Val Leu Thr
                290                 295                 300
Ser Ala Asp Gly Arg Gly Ile Lys Ile Thr Gly Ser Ile Gly Val
                305                 310                 315
Gly Ala Gly Ile Leu His Thr Glu Asn Tyr Gly Arg Leu Ser Leu
                320                 325                 330
Val Lys Asn Asp Gly Arg Asp Ile Asn Ile Ser Gly Thr Gly Leu
                335                 340                 345
Ser Ala Ile Gly Met Gly Ala Thr Asp Met Ile Ser Gln Ser Ser
                350                 355                 360
Val Ser Leu Arg Glu Ser Lys Gly Gln Ile Ser Ala Ala Asn Ala
                365                 370                 375
Asp Ala Met Gly Phe Asn Ala Tyr Asn Gly Gly Gly Ala Lys Gln
                380                 385                 390
Ile Ile Phe Ala Ser Ser Ile Ala Gly Phe Met Ser Gln Ala Gly
                395                 400                 405
Ser Gly Phe Ser Ala Gly Ser Gly Phe Ser Val Gly Ser Gly Lys
                410                 415                 420
Asn Tyr Ser Ala Ile Leu Ser Ala Ser Ile Gln Ile Val Ser Ser
                425                 430                 435
Ala Arg Ser Ile Ser Ser Thr Tyr Val Val Ser Thr Gly Ser Gly
                440                 445                 450
Phe Ser Ala Gly Ser Gly Asn Ser Gln Phe Ala Ala Leu Arg Ile
                455                 460                 465
Ser Thr Val Ser Ala His Asp Glu Thr Ala Gly Val Thr Thr Leu
                470                 475                 480
Lys Gly Ala Met Ala Val Met Asp Ile Ala Glu Thr Ala Ile Thr
                485                 490                 495
Asn Leu Asp Gln Ile Arg Ala Asp Ile Gly Ser Val Gln Asn Gln
                500                 505                 510
Ile Thr Ser Thr Ile Asn Asn Ile Thr Val Thr Gln Val Asn Val
                515                 520                 525
Lys Ser Ala Glu Ser Gln Ile Arg Asp Val Asp Phe Ala Ser Glu
                530                 535                 540
Ser Ala Asn Tyr Ser Lys Ala Asn Ile Leu Ala Gln Ser Gly Ser
                545                 550                 555
Tyr Ala Met Ala Gln Ala Asn Ser Ser Gln Gln Asn Val Leu Arg
                560                 565                 570
Leu Leu Gln
```